United States Patent [19]
Miyadera et al.

[11] 4,005,081
[45] Jan. 25, 1977

[54] 3-HETEROTHIOMETHYL-7α-METHOXY-7β-TETRAZOLYLMETHYLTHI-OACETAMIDO-3-CEPHEM DERIVATIVES

[75] Inventors: Tetsuo Miyadera, Kanagawa, Japan; Hermann Breuer; Uwe D. Treuner, both of Regensburg, Germany

[73] Assignee: E. R. Squibb & Sons, Inc., Princeton, N.J.

[22] Filed: Sept. 11, 1975

[21] Appl. No.: 612,387

[52] U.S. Cl. .......................... 260/243 C; 424/246; 260/308 D
[51] Int. Cl.² ...................................... C07D 501/56
[58] Field of Search ................ 260/243 C

[56] References Cited
FOREIGN PATENTS OR APPLICATIONS
2,129,675  12/1971  Germany

*Primary Examiner*—Nicholas S. Rizzo
*Assistant Examiner*—Diana G. Rivers
*Attorney, Agent, or Firm*—Lawrence S. Levinson; Merle J. Smith

[57]  ABSTRACT

7α-Methoxy-7β-tetrazolylmethylthioacetamido-3-cephem derivatives which have a heterothiomethyl substituent in the 3-position are novel compounds which are useful as antimicrobial agents.

8 Claims, No Drawings

3-HETEROTHIOMETHYL-7α-METHOXY-7β-TETRAZOLYLMETHYLTHIOACETAMIDO-3-CEPHEM DERIVATIVES

SUMMARY OF THE INVENTION

This invention relates to new cephalosporin derivatives which have the formula

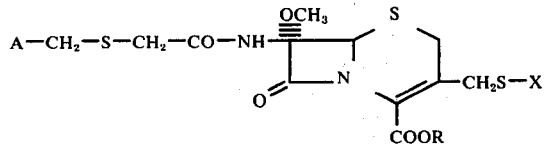

(I)

A is a tetrazole ring attached by a nitrogen atom, unsubstituted or substituted by lower alkyl.

R is hydrogen, lower alkyl, phenyl-lower alkyl, diphenyl-lower alkyl, a salt forming ion or the group

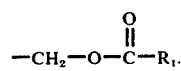

$R_1$ is lower alkyl, phenyl or phenyl-lower alkyl.

X is a five-membered heterocyclic ring containing carbon and 1 to 4 atoms selected from the group consisting of nitrogen, sulfur and oxygen unsubstituted or substituted with lower alkyl.

DETAILED DESCRIPTION OF THE INVENTION

The invention relates to new cephalosporin derivatives having the formula I above.

A represents a tetrazole ring which is attached by one of its nitrogen atoms to the carbon of the chain and which is unsubstituted or bears a lower alkyl group on the carbon.

R is hydrogen, lower alkyl, phenyl-lower alkyl, diphenyl-lower alkyl, a salt forming ion as described below or

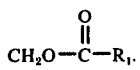

$R_1$ is lower alkyl, phenyl or phenyl-lower alkyl.

The lower alkyl groups are straight or branched chain aliphatic hydrocarbon radicals of up to seven carbon atoms, including for example, methyl, ethyl, propyl, isopropyl, butyl, isobutyl, t-butyl, etc. The one to four carbon members are preferred, especially methyl and ethyl and particularly methyl. The phenyl-lower alkyl groups include the described lower alkyl groups attached to a phenyl, for example, benzyl, phenethyl, etc., and the diphenyl-lower alkyl group includes diphenylmethyl, which is preferred, and the like.

The salt forming ions represented by R include metal ions, e.g., alkali metal ions such as sodium and potassium (which is preferred), alkaline earth metal ions such as calcium or magnesium, or an amine salt ion, for example, lower alkylamines like tri(lower alkyl)amines such as triethylamine, methylamine or (cyclo-lower alkyl)amines (especially 5–6C) such as dicyclohexylamine.

X is a five-membered heterocyclic ring containing carbon and 1 to 4 of the hetero atoms nitrogen, oxygen and sulfur, in particular, one of the heterocyclics oxadiazole, thiadiazole, thiatriazole, triazole or tetrazole, unsubstituted or bearing a lower alkyl group of the type described above, having the following configurations:

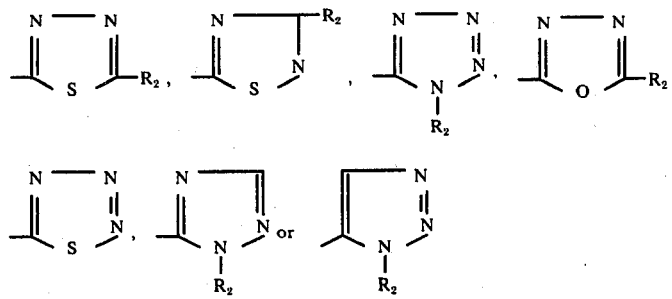

$R_2$ is hydrogen or lower alkyl, preferably lower alkyl of 1 to 4 carbons, especially 1 to 2 carbons.

Preferred embodiments of this invention are included in the examples, but expecially preferred are those wherein:

A is 1-tetrazolyl (1H-tetrazol-1-yl).

R is hydrogen, alkali metal or

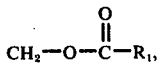

$R_1$ is lower alkyl, especially hydrogen, pivaloyloxy, sodium or potassium.

X is thiadiazole, tetrazole and their methyl substituted analogs(i.e., $R_2$ is methyl), especially 1,3,4-thiadiazole, tetrazole, 5-methyl-1,3,4-thiadiazole and 1-methyltetrazole, most especially the last two.

The new compounds of this invention are produced by the general method of reacting 7β-amino-7α-methoxycephalosporanic acid (7-AMCA), or a derivative wherein R is other than hydrogen, with a mercaptan HS-X at a pH of about 8–8.5 to obtain the derivative of the formula

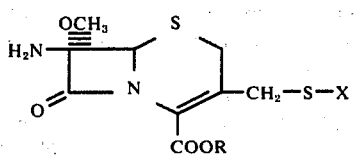

(II)

wherein R and X have the meanings defined above, R being preferably the diphenylmethyl group.

The product of formula II is then acylated on the amino group with an acid having the formula $$A-CH_2-S-CH_2-COOH \quad (III)$$

wherein A is a tetrazole ring as defined above or an active derivative.

The acid of formula III can be converted to its acid halide, e.g., by treating with oxalyl chloride or thionyl chloride, or to a mixed carbonic or other anhydride, e.g., by treating with an anhydride forming reagent such as a lower alkyl chloroformate like ethyl chloroformate, or an aryl chloroformate, etc. Carboxylic acid monoesters, acid azides, nitrophenyl esters, etc. can also be used. The reaction is effected in a solvent such as methylene chloride, chloroform, dioxane, tetrahydrofuran, dimethoxyethane, benzene, acetone, acetonitrile, dimethylformamide, or the like, at a temperature of about −20° to +20° C.

A carboxyl activating agent like dicyclohexylcarbodiimide or bisimidazole carbonyl can also be utilized.

The compound of formula II is preferably in the form of a protected ester, i.e., wherein R is diphenylmethyl, trichloroethyl, t-butyl or the like.

The reaction between the compound of formula II (or its derivative) and the acid of formula III (or its derivative) is effected, for example, by adding, at a low temperature, e.g., about 0° C. or below, the acid or derivative to the 7β-amino-7α-methoxycephalosporanic acid compound in an inert organic solvent such as chloroform, methylene chloride, dioxane, tetrahydrofuran, benzene or the like, in the presence of a tertiary organic base, e.g., lower alkylamine like triethylamine, pyridine, dimethylaniline, diethylaniline or the like. The product of the reaction is then isolated by conventional procedures, e.g., by concentration or evaporation of the solvent, filtration, recrystallization, etc.

As an alternative, the 7-AMCA can first be acylated and the product of this reaction is made to react with the mercaptan HS—X.

An especially preferred method of synthesis includes the sequence of treating a compound of the formula

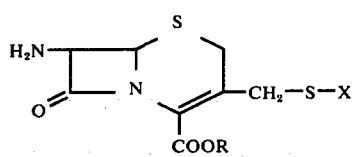

(IV)

wherein R is diphenylmethyl and X is one of the heterocyclic radicals described above, with a hydroxybenzaldehyde, e.g., a (di-lower alkyl)hydroxybenzaldehyde like 3,5-di-tert-butyl-4-hydroxybenzaldehyde, in an inert aromatic organic solvent like benzene, preferably with heating and removal of water, to obtain a Schiff's base. The latter is then added to lead dioxide, dissolved or suspended in an organic solvent like benzene at a reduced temperature of about 10° C. Methanol is added to the reaction product and the 7α-methoxy-Schiff's base derivative of IV is isolated or used directly in the next step. The 7α-methoxy derivative of the compound of formula IV is obtained from the Schiff's base by treating the latter with Girard reagent T at about ambient termperature.

This derivative is now acylated with the acid of formula III, in the form of its acid chloride, in a solvent like methylene chloride at a reduced temperature, e.g., about −10° to −20° C., in the presence of a tertiary organic base, preferably diethylaniline.

The desired final product wherein R is hydrogen is now obtained by treating the product of the last described step with trifluoroacetic acid and anisole or chloroethane at a reduced temperature, e.g., about −20° to −30° C. The product is then conventionally worked up to obtain the purified compound.

The carboxylate salts are formed by reacting the carboxyl group with a compound providing any of the salt forming ions previously described.

When R is the acyloxymethyl group

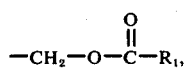

this group can be introduced at various stages, e.g., prior to or subsequent to the reaction with the acylating agent, by treatment with one or two moles of a halomethyl ester of the formula $$hal-CH_2-OCOR_1 \quad (V)$$

wherein hal is halogen, preferably chlorine or bromine, in an inert organic solvent like dimethylformamide, acetone, dioxane, benzene or the like at about ambient temperature or below.

Further process details are provided in the illustrative examples.

The acids of formula III are produced by conventional procedures such as reacting a compound of the formula $$A-CH_2-hal \quad (VI)$$

with a compound of the formula $$HS-CH_2-COOH \quad (VII)$$

in the presence of a base, then acidifying, or by reacting the compound of formula VI with an ester of a compound of formula VII, e.g., a compound of the formula $$HS-CH_2-COO-alkyl \quad (VIII)$$

in the presence of a base to obtain an ester of the formula $$A-CH_2S-CH_2-COOalkyl \quad (IX)$$

saponifying and then acidifying.

Still another method comprises reacting a compound of the formula A—H in the presence of a base with a compound of the formula $$hal-CH_2-S-CH_2-COO-alkyl \quad (X)$$

saponifying and then acidifying.

Certain of the compounds of the invention may exist in different optically active forms in the presence of an asymmetric carbon atom. The various stereoisomeric forms are within the scope of the invention.

The compounds of this invention have antibacterial activity against both gram positive and gram negative organisms such as *Staphylococcus aureus, Salmonella schottmuelleri, Escherichia coli, Streptococcus pyogenes, Enterobacter hafniae, Klebsiella pneumoniae* and *Serratia marcescens* and are useful as antibacterial agents to combat infections due to organisms such as those named above, and in general may be utilized in a manner similar to cephradine and other cephalosporins. For example, a compound of formula I or a physiologically acceptable salt thereof can be used in various mammalian species in an amount of about 2 to 50 mg/kg, daily, orally or parenterally, in single or two to four divided doses to treat infections of bacterial origin. e.g., the dosage in mice is about 5.0 mg/kg.

Up to about 500 mg. of a compound of formula I or a physiologically acceptable salt is incorporated in a dosage form such as tablet, capsule or elixir for oral administration or in a sterile aqueous vehicle for intramuscular or intravenous injection prepared according to conventional pharmaceutical practice.

The following examples are illustrative of the invention. All temperatures are on the celsius scale. They serve as models for producing additional variations in the same manner by appropriate substitution in the starting material.

EXAMPLE 1 a. 22.7 g. (0.32 mol.) of tetrazole and 58.8 ml. (0.42 mol.) of triethylamine are dissolved in 150 ml. of acetone and 64.9 g. (0.42 mol.) of chloromethylthioacetic acid methyl ester in acetone are added. This is stirred overnight and then refluxed for 5 hours. After cooling, the recipitated triethylamine hydrochloride is filtered under suction. The filtrate is evaporated to dryness, the residue is taken up in 200 ml. of dioxane and cooled to about 10°. A small additional amount of triethylamine hydrochloride is filtered off and the filtrate is again evaporated. The residue comprises 90 g. of a crude mixture of [[(1-tetrazolyl)-methyl]thio]acetic acid methyl ester and [[(2-tetrazolyl)methyl]thio]acetic acid methyl ester. The isomeric esters are separated by dissolving the mixture in methylene chloride and chromatographing over 500 g. of silica gel. Three fractions are obtained: (1) 17.7 g. of liquid [[(1-tetrazolyl)methyl]thio]acetic acid methyl ester, (2) 16.0 g. of [[(2-tetrazolyl)methyl]thio]acetic acid methyl ester, m.p. 49°–51°, and (3) 7.3 g. of a mixture of the two. Fraction 2 is recrystallized from isopropanol to obtain 14 g. of pure ester, m.p. 54°–56°.

b. 16. g. of the liquid [[(1-tetrazolyl)methyl]thio]acetic acid methyl ester, fraction 1 in part (a), are dissolved in 50 ml. of methanol and 51 ml. of a 2N solution of potassium hydroxide in methanol are added. [[(1-tetrazolyl)methyl]thio]acetic acid potassium salt crystallizes, yield of 16.5 g., m.p. 185°–188° (dec.).

c. 10 g. of the potassium salt from part (b) are dissolved in 20 ml. of water and 47 ml. of a 1N hydrochloric acid solution are added. The solution is freeze dried. By extracting with methylene chloride and concentrating, 7.0 g. of [[(1-tetrazolyl)methyl]thio]acetic acid are obtained, m.p. 98°–101°.

d. 2.1 g. (0.012 mol.) of the acid obtained in part (c) are heated at 50° with 100 ml. of thionyl chloride for 90 minutes. The reaction mixture is then refluxed for 30 minutes. The clear light solution is evaporated to dryness, taken up with 10 ml. of absolute dioxane and again evaporated. The oily residual [[(1H-tetrazol-1-yl)methyl]-thio]acetyl chloride is used without additional purification.

EXAMPLE 2 a. A solution of 129.9 g. (0.84 mol.) of chloromethylthioacetic acid methyl ester in 350 ml. of acetone is added dropwise with stirring at room temperature to a solution of 58.9 g. of 5-methyltetrazole and 98 ml. of triethylamine in 350 ml. of acetone. 1 g. of sodium iodide is added and the reaction mixture is refluxed for 3½ hours. The precipitated triethylamine hydrochloride is filtered off and the filtrate is concentrated. The residue is taken up in 600 ml. of methylene chloride, washed twice with aqueous sodium carbonate solution, dried with magnesium sulfate and the solvent is removed in a rotary evaporator. The oily residue is distilled under high vacuum. Two fractions are obtained: (1) 27.3 g. of [[(5-methyl-2-tetrazolyl)methyl]-thio]acetic acid, methyl ester, b.p. $_{0.01}$ 101°–103°; (2) 25.3 g. of [[(5-methyl-1-tetrazolyl)methyl]thio]acetic acid, methyl ester, b.p. $_{0.01}$ 165°–167°.

b. 10 ml. of ethanol are added to 20.2 g. (0.1 mol.) of [[(5-methyl-1-tetrazolyl)methyl]thio]acetic acid, methyl ester (fraction 2of part a) and 60 ml. of a 2N solution of potassium hydroxide in ethanol are added dropwise with stirring and cooling with ice water. 19.2 g. of [[(5-methyl-1-tetrazolyl)methyl]thio]acetic acid, potassium salt crystallize, m.p. 150° (dec.). This salt is recrystallized from ethanol, m.p. 150° (dec.).

c. 8.7 gl of the potassium salt obtained in part (b) are suspended in 50 ml. of benzene and 5 drops of pyridine are added. Then a solution of 9.8 g. of oxalyl chloride in 15 ml. of benzene are slowly added dropwise with stirring, keeping the temperature at about 10°. The reaction mixture is permitted to stand at room temperature for four more hours, then concentrated in vacuum. The residue is taken up in ether, filtered and the ether is evaporated in a rotary evaporator. The residual 4.9 g. of [[(5-methyl-1-tetrazolyl)methyl]thio]-acetyl chloride is used further without additional purification.

d. By substituting 5-ethyltetrazole for the 5-methyltetrazole in part (a) above, [[(5-ethyl-2-tetrazolyl)methyl]thio]-acetic acid, methyl ester, and [[5-ethyl-1-tetrazolyl)methyl]-thio]acetic acid methyl ester, are obtained.

EXAMPLE 3 a. To 20.2 g (0.1 mol.) of [[(5-methyl-2-tetrazolyl)-methyl]thio]acetic acid, methyl ester (fraction 1 of Example 2a) are added 10 ml. of ethanol and 60 ml. of a 2N solution of potassium hydroxide in ethanol are added dropwise with stirring and cooling with ice water. 21.1 g. of [[(5-methyl-2-tetrazolyl)methyl]thio]acetic acid, potassium salt, crystallize, m.p. 155° (dec.).

b. 11.3 g. (0.05 mol.) of the potassium salt obtained in part a are suspended in 75 ml. of benzene and 5 drops of pyridine are added. A solution of 12.7 g. (0.1 mol.) of oxalyl chloride in 25 ml. of benzene are slowly added dropwise with stirring, the temperature being maintained at about 10°. **The reaction mixture is stirred for 4 more hours at room temperature and concentrated in vacuum. The residue is taken up in ether, filtered and the ether is evaporated in a rotary evaporator. The residual (12 g.) crude [[(5-methyl-2H-tetrazol-2-yl)methyl]thio]acetyl chloride is used without further purification.

EXAMPLE 4

3-[[(5-Methyl-1,3,4-thiadiazol-2-yl)thio]methyl]-7β-amino-8-oxo-5-thia-1-azabicyclo[4.2.0]oct-2-ene-2-carboxylic acid A mixture of 13.6 g. (0.05 mol.) of 7-aminocephalosporanic acid (7-ACA) in 100 ml. of water and 50 ml. of acetone is brought to pH 8 with sodium hydroxide while stirring. 7.5 g (0.057 mol.) of 2-methyl-1,3,4-thiadiazole-5-thiol are added and the mixture is heated at 80° for 4 hours. After cooling to 5°, this is acidified to pH 3.5 with dilute hydrochloric acid and stirred for 15 minutes. The precipitated solid is filtered under suction and washed with acetone. This 3-[[(5-methyl-1,3,4-thiadiazol-2-yl)thio]-methyl]-7-amino-8-oxo-5-thia-1-azabicyclo[4.2.0]oct-2-ene-2-carboxylic acid is purified by dissolving in sodium bicarbonate solution and reprecipitating with 2N hydrochloric acid; yield 12.7 g., m.p. 206°.

EXAMPLE 5

3-[[(3-Methyl-1,2,4-thiadiazol-5-yl)thio]methyl]-7β-amino-8-oxo-5-thia-1-azabicyclo[4.2.0]oct-2-ene-2-2-carboxylic acid By substituting 3-methyl-1,2,4-thiadiazole-5-thiol for the 2-methyl-1,3,4-thiadiazole-5-thiol in the procedure of Example 4, 11.6 g. of 3-[[(3-methyl-1,2,4-thiadiazol-5-yl)thio]methyl]-7β-amino-8-oxo-5-thia-1-azabicyclo[4.2.0]oct-2-ene-2-carboxylic acid, m.p. 186° (dec.), are obtained.

EXAMPLE 6

3-[[(1-Methyl-1H-tetrazol-5-yl)thio]methyl]-7β-amino-8-oxo-5-thia-1-azabicyclo[4.2.0]oct-2ene-2carboxylic acid By substituting 0.057 mol. of 1-methyl-1H-tetrazole-5-thiol for the 2-methyl-1,3,4-thiadiazole-5-thiol in the procedure of Example 4, 3-[[(1-methyl-1H-tetrazol-5-yl)thio]-methyl]-7β-amino-8-oxo-5-thia-1-azabicyclo[4.2.0.]oct-2-ene-2-carboxylic acid is obtained.

EXAMPLE 7

7β-Amino-3-[[(5-methyl-1,3,4-thiadiazol-2-yl)thio]-methyl]-8-oxo-5-thia-1-azabicyclo[4.2.0]oct-2-ene-2-carboxylic acid, diphenylmethyl ester 18 g. of 7β-amino-3-[[(5-methyl-1,3,4-thiadiazol-2-yl)-thio]methyl]-8-oxo-5-thia-1azabicyclo[4.2.0.]oct-2-ene-2-carboxylic acid are suspended in 350 ml. of tetrahydrofuran. 4.1 ml. of 70% perchloric acid are added dropwise. After 30 minutes, a slightly turbid solution forms. This solution is filtered and to the filtrate is added dropwise with stirring 12 g. of diphenyldiazomethane and 20 ml. of tetrahydrofuran. After 3 hours, the reaction mixture is poured into 2 liters of absolute ether. The solid, light brown precipitate, which is the perchloric acid salt of the desired product, is dried over Kieselgel in a desiccator. To obtain the base, the perchloric acid salt is dissolved in water and treated with the calculated equivalent of potassium bicarbonate. The aqueous solution obtained is extracted with chloroform. The chloroform phase is treated with activated carbon and sodium sulfate to obtain 10 g. of the product, 7β-amino-2-[[(5-methyl-1,3,4-thiadiazol-2yl)thio]methyl]-8-oxo-5-thia-1-azabicyclo[4.2.0]oct-2ene-2carboxylic acid, diphenylmethyl ester, as a light brown powder, m.p. 157°–159°. The product is recrystallized from tetrahydrofuran/petroleum ether.

7β-Amino-3-[[(3-methyl-1,2,4-thiadiazol-5-yl)thio]-methyl]-8-oxo-5-thia-1-azabicyclo[4.2.0]oct-2-ene-2-carboxylic acid, diphenylmethyl ester is similarly obtained by substituting the product of Example 5.

EXAMPLE 8

7β-Amino-3-[[(1-methyl-1H-tetrazol-5-yl)thio]methyl]-8-oxo-5-thia-1-azabicyclo[4.2.0]oct-2-ene-2carboxylic acid, diphenylmethyl ester The product, 7β-amino-3-[[(1-methyl-1H-tetrazol-5-yl)-thio]methyl]8-oxo-5-thia-1-azabicyclo[4.2.0]oct-2-ene-2-carboxylic acid, diphenylmethyl ester, m.p. 168°–169° (dec.), is obtained by the procedure of Example 7 utilizing as starting material 7β-amino-3-[[(1-methyl-1H-tetrazol-5-yl)-thio]methyl]-8-oxo-5-thia-1-azabicyclo[4.2.0]oct-2-ene-2-carboxylic acid.

EXAMPLE 9

7α-Methoxy-7β-(3,5-di-tert-butyl-4-hydroxybenzylideneamino)-3-[[(1-methyl-1H-tetrazol-5-yl)thio]-methyl]-8-oxo-5-thia-1-azabicyclo[4.2.0]oct-2-ene-2-carboxylic acid, diphenylmethyl ester A mixture of 4.5 g. (9.10 mmol.) of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester, and 2.25 g. (9.60 mmol.) of 3,5-di-tert-butyl-4-hydroxybenzaldehyde in 67 ml. of benzene is heated under reflux for 1.5 hr. with azeotropic removal of the water formed. The resulting solution of the Schiff's base is added with cooling at 10° and vigorous stirring to a suspension of lead dioxide in 100 ml. of benzene freshly prepared from lead tetraacetate (18 g.). After the mixture has been stirred for 60 minutes, the inorganic material is filtered off, 100 ml. of methanol is added to the filtrate and the mixture is allowed to stand overnight at room temperature. The solvent is evaporated to dryness in vacuo leaving 7α-methoxy-7β-(3,5-di-tert-butyl-4-hydroxybenzylideneamino)-3-[[(1-methyl-1H-tetrazol-5-yl)thio]methyl]-8-oxo-5-thia-1-azabicyclo[4.2.0]oct-2-ene-2-carboxylic acid, diphenylmethyl ester as an amorphous powder (6.3 g.). The crude product is used for the subsequent reaction without further purification.

EXAMPLE 10

7β-Amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester A solution of 6.0 g. Girard reagent T in 35 ml. of methanol is added to a solution of the Schiff's base from Example 9 in 35 ml. of ethyl acetate at room temperature and the mixture is stirred for 1 hour. After the reaction mixture is concentrated to ca. 15 ml. in vacuo, ethyl acetate and cold water are added. The mixture is shaken and the organic layer is separated. The aqueous layer is extracted with ethyl acetate and the combined ethyl acetate solution is washed with cold water and dried over sodium sulfate. The solvent is evaporated to dryness in vacuo to give 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester as an amorphous powder (2.3 g.). NMR (in CDCl₃) δ: 2.17 (2H, broad peak, NH₂), 3.51 (3H, singlet, OCH₃), 3.60 (2H, singlet, —CH₂— at 2 position), 3,83 (3H, singlet, N—CH₃), 4.28 and 4.53 (2H, AB-quartet, J=13.5 Hz, —CH₂S-tetrazole), 4,87 (1H, singlet,

at 6 position), 6.97 (1H, singlet, Ph₂CH—) and 7.20–7.53 (10H, multiplet, Ph₂).

EXAMPLE 11

7α-Methoxy-3-[[(1-methyl-1H-tetrazol-5-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid, diphenylmethyl ester To 2.1 g. (4 mmol.) of 7β-amino-7α-methoxy-3-[[(1-methyl-1H-tetrazol-5-yl)thio]methyl]-8-oxo-5-thia-1-azabicyclo[4.2.0]-oct-2-ene-2-carboxylic acid, diphenylmethyl ester, in 20 ml. of tetrahydrofuran are added a solution of 656 mg. (4.4 mmol.) of N,N-diethylaniline in 5 ml. of tetrahydrofuran and a solution of 848 mg. (4.4 mmol.) of [[(1H-tetrazol-1-yl)methyl]thio]acetyl chloride in 8 ml. of tetrahydrofuran at −10°. After stirring for 30 minutes, the mixture is poured into ice water and extracted with ethyl acetate. The extract is washed successively with 5% hydrochloric acid, 5% sodium bicarbonate and water, then dried over sodium sulfate. The solvent is evaporated in vacuo and the residue is purified by preparative TLC (silica gel, AcOEt) to give the acyl derivative (IV, 1.26 g., 46%). NMR (in CDCl₃): 3.53 (3H, singlet, —OCH₃), 3.40—3.63 (2H and 2H, —CH₂— at 2 position and —SCH₂CO—), 3.83 (3H, singlet, NCH₃), 4.20 and 4.47 (2H, AB-quartet, J=14.0 Hz, —CH₂S-tetrazole), 5.07 (1H, singlet, —CH— at 6 position), 5.81 (2H singlet, —SCH₂-tetrazole), 6.90 (1H, singlet, Ph₂CH—), 7.16—7.60 (10H, multiplet, Ph₂), 7.67 (1H, broad singlet, NH), and 8.53 (1H, singlet, hydrogen of tetrazole).

EXAMPLE 12

7α-Methoxy-3-[[(1-methyl-1H-tetrazol-5-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid 3 ml. of trifluoroacetic acid is added to a solution of 1.256 g. of the product of Example 11 in 30 ml. of dichloroethane at −13° and the mixture is stirred for 30 minutes. After removal of the solvent and the trifluoroacetic acid, the residue is dissolved in 10% dipotassium hydrogen phosphate solution and the aqueous solution is washed with ethyl acetate. The aqueous solution is saturated with sodium chloride and then made acidic (pH=2.1) with hydrochloric acid while cooling. The acidic solution is extracted with ethyl acetate three times and the extract is dried over sodium sulfate. The solvent is evaporated in vacuo and the residue is purified by preparative TLC (silica gel, CHCl₃—MeOH (2:1)). The acid separated by the TLC is dissolved in 10% dipotassium hydrogen phosphate solution and washed with ethyl acetate. The aqueous phase is made acidic (pH 2.1) and extracted with ethyl acetate which is dried and evaporated. The residue is dissolved in benzene and freeze-dried to give colorless crystals of 7α-methoxy-3-[[(1-methyl-1H-tetrazol-5-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid (557 mg., 60%). Anal. Calcd. for C₁₅H₁₈N₁₀O₅S₃ . 2/3C₆H₆: C, 40.27; H, 3.91; N, 24.72; S, 16.97. Found: C, 40.29; H, 4.12; N, 23.97; S, 16.86. IR(Nujol) cm⁻¹: 3250, 1775, 1720 and 1690. NMR (in DMF-d₆) (100 Mc)δ: 3.50 (3H, singlet, OCH₃), 3.69 (2H, singlet, —SCH₂CO—), 3.61 and 3.84 (2H, AB-quartet, J=18.0 Hz, —CH₂— at 2 position), 4.02(3H, singlet, NCH₃), 4,32 and 4.54 (2H, AB-quartet, J=13.0 Hz,—CH₂S—tetrazole), 5.14(1H, singlet, —CH— at 6 position),6.08(2H, singlet, —SCH₂-tetrazole), 9.00 (1H, singlet, hydrogen of tetrazole), and 9.48 (1H, broad singlet, —CONH—).

EXAMPLE 13

7α-Methoxy-3-[[(1-methyl-1H-tetrazol-5-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid, sodium salt 1.3 g. of 7α-methoxy-3-[[(1-methyl-1H-tetrazol-5-yl)thio]methyl]-8-oxo-7β-[[[(1H-tetrozol-1-ylmethyl)thio]-acetyl]amino]-5-thia-1-azabicyclo[4.2.0]oct-2-ene-2-carboxylic acid are dissolved in 15 ml. of acetone. 29 ml. of 0.1 N sodium bicarbonate solution are added, the acetone is distilled off under vacuum and the residue is filtered. The filtrate is freeze dried, to obtain 7α-methoxy-3-[[(1-methyl-1H-tetrazol-5-yl)thio]methyl]-8-oxo-7β-[[[(1H-tetrazol-1-ylmethyl)thio]acetyl]amino]-5-thia-1-azabicyclo-[4.2.0]oct-2-ene-2-carboxylic acid, sodium salt.

EXAMPLE 14

7α-methoxy-7β-(3,5-di-tert-butyl-4-hydroxybenzylideneamino)-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester A mixture of 9.0 g. (17.6 mmol.) of 7-amino-3-[[(5-methyl-1,3,4-thiadiazol-2-yl)thio]methyl]-8-oxo-5-thia-1-azabicyclo-[4.2.0]oct-2-ene-2-carboxylic acid, diphenylmethyl ester and 4.34 g. (18.5 mmol.) of 3,5-di-tert-butyl-4-hydroxybenzaldehyde in 135 ml. of benzene is heated under reflux for 1.5 hours with azeotropic removal of the water formed. The resulting solution of the Schiff base is added with cooling at 10° and vigorous stirring to a suspension of lead dioxide in 200 ml. of benzene freshly prepared from lead tetraacetate (35 g.). After the mixture has been stirred for 60 minutes, the inorganic material is filtered off and 300 ml. of methanol is added to the filtrate and the mixture is allowed to stand overnight at room temperature. The solvent is evaporated to dryness in vacuo leaving 7α-methoxy-7β-(3,5-di-tert-butyl-4-hydroxybenzylideneamino)-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester as an amorphous powder (13.9 g.). The crude product is used for the subsequent reaction without further purification.

EXAMPLE 15

7β-Amino-7α-methoxy-3-[[(5-methyl-1,3,4-thiadiazol-2-yl)thio]-methyl]-8-oxo-5-thia-1-azabicyclo[4.2.0]oct-2-ene-2-carboxylic acid, diphenylmethyl ester A solution of 6.0 g. of Girard reagent T in 96 ml. of methanol is added to a solution of 9.0 g. of the product of Example 14 in 96 ml. of ethyl acetate at room temperature and the mixture is stirred for 1 hour. After the reaction mixture is concentrated to ca. 50 ml. in vacuo, ethyl acetate and cold water are added. The mixture is shaken and the organic layer is separated. The aqueous layer is extracted with ethyl acetate and the combined ethyl acetate solution is washed with cold water and dried over sodium sulfate. The solvent is evaporated to dryness in vacuo to give 7β-amino-7α-methoxy-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester as an amorphous powder (5.7 g.). NMR ( in CDCl$_3$) δ: 2.25 (2H, broad peak,—NH$_2$), 2.64 (3H, singlet, —CH$_3$), 3.47 (3H, singlet, —OCH$_3$), 3.53 (2H, singlet, —CH$_2$— at 2 position), 4.28 and 4.54 (2H, AB-quartet, J=13.0 Hz, —CH$_2$—S— thiadiazole, 4.80 (1H, singlet, —CH— at 6-position), 6.90 (1H, singlet, CHPh$_2$), and 7.20–7.60 (10H, multiplet, Ph$_2$C—).

EXAMPLE 16

7α-Methoxy-3-[[(5-methyl-1,3,4-thiadiazol-2-yl)thio]-methyl]-8-oxo-7β-[[[(1H-tetrazol-1-ylmethyl)thio]acetyl]amino]-5-thia-1-azabicyclo[4.2.0]oct-2-ene-2-carboxylic acid, diphenylmethyl ester To a solution of 1.08 g. (2 mmol.) of 7β-amino-7α-methoxy-3-[[(5-methyl-1,3,4-thiadiazol-2-yl)thio]methyl]-8-oxo-5-thia-1-azabicyclo[4.2.0]oct-2-ene-2-carboxylic acid, diphenylmethyl ester in 10 ml. of tetrahydrofuran (10 ml.) are added a solution of 328 mg. (2.2 mmol.) of N,N-diethylaniline in 2 ml. of tetrahydrofuran and a solution of 424 mg. (2.2 mmol.) of [[(1H-tetrazol-1-yl)methyl]thio]acetyl chloride in 4 ml. of tetrahydrofuran at −14°. After stirring for 30 minutes, the mixture is poured into ice water and extracted with ethyl acetate. The extract is washed successively with 5% hydrochloric acid, water, 5% sodium bicarbonate and water, and dried over sodium sulfate. The solvent is evaporated in vacuo and the residue is purified by preparative TLC (silica gel, ethyl acetate) to give 7α-methoxy-3-[[(5-methyl-1,3,4-thiadiazol-2-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid, diphenylmethyl ester (109 g., 78.5%). NMR (in CDCl$_3$) δ: 2.67 (3H, singlet, —CH$_3$), 3.40—3.67 (2H and 2H, not clear due to overlapping, —CH$_2$— at 2 position and —S—CH$_2$—CO—), 3.55 (3H, singlet, —OCH$_3$), 4.21 and 4.60 (AB-quartet, J=13.0 Hz, —CH$_2$—S-thiadiazole), 5.10 (1H, singlet, $$-\overset{|}{\underset{}{\text{CH}}}-$$

at 6 position), 5.83 (2H, singlet, —S—CH$_2$—tetrazole), 6.95 (1H, singlet, Ph$_2$CH—), 7.16—7.60 (10H, multiplet, Ph$_2$—C—), 7.70 (1H, broad singlet, —NH—), and 8.53 (1H, singlet, hydrogen of tetrazole).

EXAMPLE 17

7α-Methoxy-3-[[(5-methyl-1,3,4-thiadiazol-2-yl)thio]-methyl]-8-oxo-7β-[[[(1H-tetrazol-1-ylmethyl)thio]acetyl]amino]-5-thia-1-azabicyclo[4.2.0]oct-2-ene-2-carboxylic acid 3 ml. of trifluoroacetic acid is added to a solution of 1.09 g. (1.6 mmol.) of the product of Example 16 in 30 ml. of dichloroethane at −14° C and the mixture is stirred for 30 minutes. After removal of the solvent and the trifluoroacetic acid, the residue is dissolved in 10% dipotassium hydrogen phosphate solution and the aqueous solution is washed with ethyl acetate. The aqueous solution is saturated with sodium chloride and then made acidic (pH = 2.1) with hydrochloric acid with cooling. The acidic solution is extracted with ethyl acetate three times and the extract is dried over sodium sulfate. The solvent is evaporated in vacuo and the residue is purified by preparative TLC (silica gel, CHCl$_3$—MeOH (2:1)). The acid separated by the TLC is dissolved in 10% dipotassium hydrogen phosphate solution, acidified to pH 2.5 with 10% hydrochloric acid solution and extracted with ethyl acetate. After drying over sodium sulfate, the ethyl acetate solution is evaporated under reduced pressure. To the residue is added benzene, which is again evaporated in vacuo to give colorless crystals (327 mg.) of 7α-methoxy-3-[[(5-methyl-1,3,4-thiadiazol-2-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid.

Anal. Calcd. for C$_{16}$H$_{18}$N$_8$O$_5$S$_4$ . H$_2$O . ½C$_6$H$_6$: C, 38.83; H, 3.95; N, 19.07; S, 21.82. Found: C, 39,29; H, 3.90; N, 18.81; S, 21.63. IR (KBr)cm$^{-1}$: 3325, 1775 and 1685. NMR (in CD$_3$SOCD$_3$) (100 Mc) δ: 2.67 (3H, singlet, —CH$_3$), 3.40 (3H, singlet, —OCH$_3$), 3.50 (2H, singlet, —SCH$_2$CO—), 3.42 and 3.72 (2H, AB-quartet, J=18.0 Hz, —CH$_2$— at 2 position), 4.17 and 4.51 (2H, AB-quartet, J=13.0 Hz, —CH$_2$—S-thiadiazole), 5.12 (1H, singlet, $$-\overset{|}{\underset{}{\text{CH}}}-$$

at 6 position), 5.96 (2H, singlet, —S—CH$_2$—tetrazole), 9.01 (1H, singlet, hydrogen of tetrazole), 9.49 (1H, broad singlet, —CONH—).

By substituting 7-amino-3-[[(3-methyl-1,2,4-thiadiazol-5-yl)thio]methyl]-8-oxo-5-thia-1-azabicyclo[4.2.0]oct-2-ene-2-carboxylic acid, diphenylmethyl ester for the starting material in Example 14 and continuing as in Examples 15 to 17, 7α-methyl-3-[[(3-methyl-1,2,4-thiadiazol-5-yl)thio]methyl]-8-oxo-7β-[[[(1H-tetrazol-1-methyl)thio]acetyl]amino]-5-thia1-azabicyclo[4.2.0]oct-2-ene-2-carboxylic acid is obtained.

EXAMPLES 18—38

The products in Examples 18 to 38 below are obtained by the procedures of Examples 11 and 12 (and Example 13 to obtain a salt) by reacting either

[[(1H-tetrazol-1-yl)methyl]thio]acetyl chloride,
[[(2H-tetrazol-2-yl)methyl]thio]acetyl chloride,
[[(5-methyl-1H-tetrazol-1-yl)methyl]thio]acetyl chloride,

[[(5-methyl-2H-tetrazol-2-yl)methyl]thio]acetyl chloride,
[(5-ethyl-1-tetrazolylmethyl)thio]acetyl chloride, or
[(5-ethyl-2-tetrazolylmethyl)thio]acetyl chloride with the diphenylmethyl ester of the following (7-AMCA=7β-amino-7α-methoxycephalosporanic acid):

7-amino-7α-methoxy-3-[[(5-methyl-1,3,4-thiadiazolyl-2-yl)thio]methyl]-8-oxo-5-thia-1-azabicyclo-[4.2.0]oct-2-ene-2-carboxylic acid
3-[[(1-methyl-1H-tetrazol-5-yl)thio]methyl]-7-AMCA
3-[[(1,3,4-oxadiazol-2-yl)thio]methyl]-7-AMCA
3-[[2-ethyl-1,3,4-oxadiazol-5-yl)thio]methyl]-7AMCA
3-[[(1,2,3,4-tetrazol-5-yl)thio]methyl]-7-AMCA
3-[[(1-ethyl-1H-tetrazol-5-yl)thio]methyl]-7-AMCA
3-[[(1,2,4-thiadiazol-3-yl)thio]methyl]-7-AMCA
3-[[[(5-butyl-1,2,4-thiadiazol-3-yl)thio]methyl]-7-AMCA
3-[[2-methyl-1,3,4-oxadiazol-5-yl)thio]methyl]-7-AMCA
3-[[(1,3,4-thiadiazol-2-yl)thio]methyl]-7-AMCA
3-[[(1,2,3,4-thiatriazol-5-yl)thio]methyl]-7-AMCA
3-[[(1,2,4-triazol-5-yl)thio]methyl]-7-AMCA
3-[[(1-methyl-1,2,4-triazol-5-yl)thio]methyl]-7-AMCA

EXAMPLE

7α-methoxy-3-[[(1,3,4-thiadiazol-2-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid
7α-methoxy-3-[[(1,3,4-oxadiazol-2-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid    7α-methoxy-3-[[(2-ethyl-1,3,4-oxadiazol-5-yl)thio]-methyl]-8-oxo-7β-[[[(2H-tetrazol-2-ylmethyl)thio]acetyl]-amino]-5-thia-1-azabicyclo[4.2.0]oct-2-ene-2-carboxylic acid
7α-methoxy-3-[[(1-methyl-1,2,4-triazol-5-yl)thio]methyl]-8-oxo-7β-[[[(1H-tetrazol-1-ylmethyl)thio]acetyl]amino]-5-thia-1-azabicyclo[4.2.0]oct-2-ene-2-carboxylic acid

EXAMPLE

7α-methoxy-3-[[(1,2,4-triazol-5-yl)thio]methyl]-8-oxo-7β-[[[(2H-tetrazol-2-ylmethyl)thio]acetyl]amino]-5-thia-1-azabicyclo[4.2.0]oct-2-ene-2-carboxylic acid.
7α-methoxy-3-[[(1,2,3,4-thiatriazol-5-yl)thio]methyl]-7β-[[[(5-methyl-1H-tetrazol-1-ylmethyl)thio]acetyl]amino]-8-oxo-5-thia-1-azabicyclo[4.2.0]oct-2-ene-2-carboxylic acid
7α-methoxy-3-[[(1,2,4-thiadiazol-3-yl)thio]methyl]-7β-[[[(5-ethyl-1H-tetrazolyl-1-ylmethyl)thio]acetyl]amino]-8-oxo-5-thia-1-azabicyclo[4.2.0]oct-2-ene-2-carboxylic acid
7α-methoxy-3-[[(1,2,4-thiadiazol-3-yl)thio]methyl]-8-oxo-7β-[[[(2H-tetrazol-2-ylmethyl)thio]acetyl]amino]-5-thia-1-azabicyclo[4.2.0]oct-2-ene-2-carboxylic acid and sodium salt
7α-methoxy-3-[[(5-butyl-1,2,4-thiadiazol-3-yl)thio]-methyl]-7β-[[[(5-ethyl-2-tetrazolylmethyl]thio]acetyl]amino]-8-oxo-5-thia-1-azabicyclo[4.2.0]oct-2-ene-2-carboxylic acid
7α-methoxy-3-[[(2-methyl-1,3,4-oxadiazol-5-yl)thio]-methyl]-8-oxo-7β-[[[(2H-tetrazol-2-ylmethyl)thio]acetyl]amino]-5-thia-1-azabicyclo[4.2.0]oct-2-ene-2-carboxylic acid
7α-methoxy-3-[[(1,2,3,4-thiatriazol-5-yl)thio]methyl]-8-oxo-7β-[[[(1H-tetrazol-1-ylmethyl)thio]acetyl]amino]-5-thia-1-azabicyclo[4.2.0]oxt-2-ene-2-carboxylic acid and benzoyloxymethyl ester
7α-methoxy-3-[[(1,2,4-triazol-5-yl)thio]methyl]-7β-[[[(5-ethyl-2-tetrazolylmethyl)thio]acetyl]amino]-8-oxo-5-thia-1-azabicyclo[4.2.0]oct-2-ene-2-carboxylic acid and phenylacetoxymethyl ester

EXAMPLE

7α-methoxy-3-[[(2-methyl-1,3,4-oxadiazol-5-yl)-thio]methyl]-7β-[[[(5-methyl-1H-tetrazol-1-ylmethyl)-thio]acetyl]amino]-8-oxo-5-thia-1-azabicyclo[4.2.0]oct-2-ene-2-carboxylic acid
7α-methoxy-3-[[(1-ethyl-1H-tetrazol-5-yl)thio]methyl]-7β-[[[(5-methyl-1H-tetrazol-1-methyl)thio]acetyl]amino]-8-oxo-5-thia-1-azabicyclo[4.2.0]oct-2-ene-2-carboxylic acid
7α-methoxy-3-[[(1-ethyl-1H-tetrazol-5-yl)thio]methyl]-8-oxo-7β-[[[(2H-tetrazol-2-ylmethyl)thio]acetyl]amino]-5-thia-1-azabicyclo[4.2.0]oct-2-ene-2-carboxylic acid and cyclohexylamine salt
7α-methoxy-3-[[[5-methyl-1,3,4-thiadiazol-2-yl]thio]-methyl]-8-oxo-7β-[[[(5-methyl-1-tetrazolylmethyl)thio]-acetyl]amino]-5-thia-1-azabicyclo[4.2.0]oct-2-ene-2-carboxylic acid
7α-methoxy-3-[[(5-methyl-1,3,4-thiadiazol-2-yl)thio]-methyl]-7β-[[[(5-ethyl-2-tetrazolylmethyl)thio]acetyl]-amino]-8-oxo-5-thia-1-azabicyclo[4.2.0]oct-2-ene-2-carboxylic acid and potassium salt
7α-methoxy-3-[[(1,3,4-oxadiazol-2-yl)thio]methyl]-7β-[[[(5-ethyl-1H-tetrazol-1-ylmethyl)thio]acetyl]amino]methyl]-8-oxo-5-thia-1-azabicyclo[4.2.0]oct-2-ene-2-carboxylic acid and sodium salt
7α-methoxy-3-[[(1-methyl-1H-tetrazol-5-yl)thio]methyl]-8-oxo-7β-[[[(5-methyl-2H-tetrazol-2-ylmethyl)thio]acetyl]amino]-5-thia-1-azabicyclo[4.2.0]oct-2-ene-2-carboxylic acid and pivaloyloxymethyl ester

EXAMPLE

7α-methoxy-3-[[(1-methyl-1H-tetrazol-5-yl)thio]methyl]-8-oxo-7β-[[[(2H-tetrazol-2-ylmethyl)thio]acetyl]amino]-5-thia-1-azabicyclo[4.2.0]oct-2-ene-2-carboxylic acid and triethylamine salt
7α-methoxy-3-[[(5-methyl-1,3,4-thiadiazol-2-yl)thio]-methyl]-8-oxo-7β-[[[(2H-tetrazol-2-ylmethyl)thio]acetyl]amino]-5-thia-1-azabicyclo[4.2.0]oct-2-ene-2-carboxylic acid and potassium salt
7α-methoxy-3-[[(1,2,3-triazol-5-yl)thio]methyl]-7β-[[[(5-methyl-1H-tetrazol-1-ylmethyl)thio]acetyl]amino]-8-oxo-5-thia-1-azabicyclo[4.2.0]oct-2-ene-2-carboxylic acid and sodium salt.

What is claimed is:
1. A compound of the formula

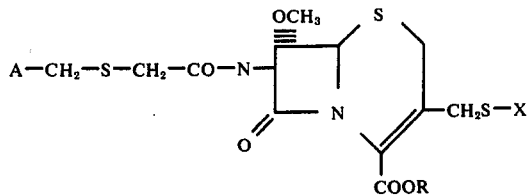

wherein

A is a tetrazole ring attached by a nitrogen atom, unsubstituted or substituted by lower alkyl;

R is hydrogen, lower alkyl, phenyl-lower alkyl, diphenyl-lower alkyl, alkali metal, alkaline earth metal, lower alkylamine, tri (lower alkyl) amine, ($C_5$-$C_6$-cyclo-lower alkyl)amine or or $-CH_2O-\overset{\overset{O}{\|}}{C}-R_1$;

$R_1$ is lower alkyl, phenyl or phenyl-lower alkyl; and
X is one of the heterocyclic rings oxadiazoloyl, thiadiazolyl, thiatriazolyl, triazolyl or tetrazolyl, unsubstituted or substituted with lower alkyl;
said lower alkyl groups having up to seven carbon atoms.

2. A compound as in claim 1 wherein A is 1-tetrazolyl.

3. A compound as in claim 1 wherein X is 1-methyl-1H-tetrazol-5-yl.

4. A compound as in claim 1 wherein X is 5-methyl-1,3,4-thiadiazol-2-yl.

5. A compound as in claim 1 wherein A is 1-tetrazolyl; R is hydrogen, alkali metal or $CH_2-O-\overset{\overset{O}{\|}}{C}-R_1$;

$R_1$ is lower alkyl; and X is thiadiazolyl, (lower alkyl) thiadizolyl, tetrazolyl or (lower alkyl) tetrazolyl.

6. A compound as in claim 1 wherein A is 1H-tetrazol-1-yl; R is hydrogen and X is 1-methyl-1H-tetrazol-5-yl.

7. A compound as in claim 1 wherein A is 1H-tetrazol-1-yl; R is sodium and X is 1-methyl-1H-tetrazol-5-yl.

8. A compound as in claim 1 wherein A is 1H-tetrazol-1-yl; R is hydrogen and X is 5-methyl-1,3,4-thiadiazol-2-yl.

* * * * *